US010765750B2

(12) United States Patent
Endo

(10) Patent No.: US 10,765,750 B2
(45) Date of Patent: *Sep. 8, 2020

(54) PHARMACEUTICAL COMPOSITION CONTAINING PYRIDYLAMINOACETIC ACID COMPOUND

(71) Applicant: SANTEN PHARMACEUTICAL CO., LTD., Osaka-shi, Osaka (JP)

(72) Inventor: Yoko Endo, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/658,585

(22) Filed: Oct. 21, 2019

(65) Prior Publication Data
US 2020/0046839 A1 Feb. 13, 2020

Related U.S. Application Data

(63) Continuation of application No. 16/173,299, filed on Oct. 29, 2018, now Pat. No. 10,485,872, which is a continuation of application No. 15/204,507, filed on Jul. 7, 2016, now Pat. No. 10,149,908, which is a continuation of application No. PCT/JP2015/050334, filed on Jan. 8, 2015.

(30) Foreign Application Priority Data

Jan. 10, 2014 (JP) ................. 2014-002810

(51) Int. Cl.
A61K 47/18 (2017.01)
A61K 47/22 (2006.01)
A61K 31/444 (2006.01)
A61K 9/00 (2006.01)
A61K 47/26 (2006.01)
A61K 47/44 (2017.01)
A61K 47/12 (2006.01)
A61K 47/02 (2006.01)

(52) U.S. Cl.
CPC .......... A61K 47/183 (2013.01); A61K 9/0048 (2013.01); A61K 31/444 (2013.01); A61K 47/22 (2013.01); A61K 47/26 (2013.01); A61K 47/44 (2013.01); A61K 47/02 (2013.01); A61K 47/12 (2013.01); Y02A 50/465 (2018.01)

(58) Field of Classification Search
CPC .................................................. A61K 47/183
See application file for complete search history.

(56) References Cited

U.S. PATENT DOCUMENTS

| 4,960,799 A | 10/1990 | Nagy |
| 5,631,287 A | 5/1997 | Schneider et al. |
| 5,998,488 A | 12/1999 | Shinohara et al. |
| 6,235,781 B1 | 5/2001 | Weiner et al. |
| 8,685,986 B2 | 4/2014 | Hagihara et al. |
| 9,415,038 B2 | 8/2016 | Shams et al. |
| 10,149,908 B2* | 12/2018 | Endo ............... A61K 47/44 |
| 10,485,872 B2* | 11/2019 | Endo ............... A61K 31/444 |
| 2002/0009507 A1 | 1/2002 | Weimer et al. |
| 2002/0165254 A1 | 11/2002 | Kis et al. |
| 2011/0054172 A1 | 3/2011 | Iwamura et al. |
| 2012/0190852 A1* | 7/2012 | Hagihara ........... C07D 417/12 544/333 |
| 2012/0263803 A1 | 10/2012 | Mashima et al. |
| 2013/0331458 A1 | 12/2013 | Miyano et al. |
| 2014/0018350 A1 | 1/2014 | Kirihara et al. |
| 2014/0018396 A1 | 1/2014 | Kirihara et al. |
| 2015/0072951 A1 | 3/2015 | Sakatani et al. |
| 2015/0196541 A1 | 7/2015 | Shams et al. |
| 2016/0317512 A1 | 11/2016 | Endo |
| 2016/0317664 A1 | 11/2016 | Endo |
| 2016/0324838 A1 | 11/2016 | Shams et al. |
| 2018/0169079 A1 | 6/2018 | Shams et al. |
| 2019/0105310 A1 | 4/2019 | Shams et al. |

FOREIGN PATENT DOCUMENTS

| CA | 2878370 A1 | 1/2014 |
| CN | 102448940 A | 5/2012 |
| EP | 2415763 A1 | 2/2012 |
| EP | 3093018 A1 | 11/2016 |

(Continued)

OTHER PUBLICATIONS

Polyoxyl Castor Oil Polyoxyl Hydrogenated Castor Oil, Summary Report, The European Agency for the Evaluation of Medicinal Products, EMEA/MRL/614/99-FINAL, Jun. 1999, available at https://www.ema.europa.eu/en/documents/mrl-report/polyoxyl-castor-oil-polyoxyl-hydrogenated-castor-oil-summary-report-committee-veterina.*
U.S. Appl. No. 16/711,706, filed Jan. 2014, Endo; Yoko.*
U.S. Appl. No. 15/204,475, filed Jan. 2014, Endo; Yoko.*
Fouquet et al, Journal of Oleo Science, ISSN 1347-3352 online, pp. 1-12, Aug. 8, 2017.*
"Packaging of Ophthalmic and parenteral products," Published on Mar. 29, 2012.
CN Office Action corresponding to Application No. 20150003056.5, dated Jun. 16, 2017.

(Continued)

Primary Examiner — Svetlana M Ivanova
(74) Attorney, Agent, or Firm — Cantor Colburn LLP

(57) ABSTRACT

The purpose of the present invention is to provide a pharmaceutical composition that comprises a specific compound and exhibits a superior preservation efficacy, the specific compound being stable within the pharmaceutical composition, and to provide methods for improving the stability of the specific compound within the pharmaceutical composition and the preservation efficacy of the pharmaceutical composition. The pharmaceutical composition according to the present invention comprises isopropyl (6-{[4-(pyrazol-1-yl)benzyl](pyridin-3-ylsulfonyl)aminomethyl}pyridin-2-ylamino)acetate or a salt thereof, and further comprises edetic acid or a salt thereof.

12 Claims, No Drawings

(56) References Cited

FOREIGN PATENT DOCUMENTS

| | | |
|---|---|---|
| EP | 3093019 A1 | 11/2016 |
| EP | 3093021 A1 | 11/2016 |
| JP | H11500122 A | 1/1999 |
| JP | 2002509101 A | 3/2002 |
| JP | 2002356420 A | 12/2002 |
| JP | 3631255 B2 | 3/2005 |
| JP | 2009114183 A | 5/2009 |
| JP | 2010100652 A | 5/2010 |
| JP | 2011057633 A | 3/2011 |
| JP | 2012180346 A | 9/2012 |
| JP | 2013151548 A | 8/2013 |
| JP | 2014019650 A | 2/2014 |
| JP | 6012775 B2 | 10/2016 |
| TW | 201340960 A | 10/2013 |
| WO | 9729752 A1 | 8/1997 |
| WO | 2009113600 A1 | 9/2009 |
| WO | 2010113957 A1 | 10/2010 |
| WO | 2012141334 A1 | 10/2012 |
| WO | 2013146649 A1 | 10/2013 |
| WO | 2014010654 A2 | 1/2014 |
| WO | 2014010354 A2 | 6/2016 |

OTHER PUBLICATIONS

European Search Report corresponding to Application No. 15735316.0-1468/3093019 PCT/JP2015050334; dated Jun. 23, 2017.

European Search Report corresponding to Application No. 15735607.2-1468/3093021 PCT/JP2015050333; dated Jun. 23, 2017.

IN Office Action corresponding to Application No. 201617026272; dated Jun. 19, 2019.

International Search Report corresponding to Application No. PCT/JP2015/050333; dated Mar. 31, 2015.

International Search Report corresponding to Application No. PCT/JP2015/050334; dated Mar. 31, 2015, with English translation.

IP Office of Singapore Written Opinion corresponding to Application No. 11201605366Q; dated May 15, 2017.

Notification of Reasons for Refusal issued to JP Patent Application No. 2015-002272, dated Aug. 14, 2018.

Notification of Reasons for Refusal issued to JP Patent Application No. 2016-181739; dated Aug. 28, 2018.

Polyoxyl Castor Oil Polyoxyl Hydrogenated Castor Oil, Summary Report, The European Agency for the Evaluation of Medicinal Products, EMEA/MRL/614/99-FINAL, Jun. 1999; 3 pages.

SIPO Office Action corresponding to Application No. 201580003108.9; dated Aug. 4, 2017.

Substantive Examination Report issued to PH Patent Application No. 1/2016/501328, dated Aug. 17, 2018.

Taiwanese Office Action corresponding to Application No. 104100528; dated Jun. 19, 2018.

USPTO Final Office Action corresponding to U.S. Appl. No. 15/204,475; dated Apr. 11, 2018.

USPTO Non-Final Office Action corresponding to U.S. Appl. No. 15/204,475; dated Nov. 2, 2018.

USPTO Non-Final Office Action corresponding to U.S. Appl. No. 15/204,475; dated Sep. 22, 2017.

USPTO Non-Final Office corresponding to U.S. Appl. No. 16/173,299; dated Mar. 28, 2019.

U.S. Non-Final Office Action corresponding to U.S. Appl. No. 15/204,507; dated Oct. 3, 2017.

* cited by examiner

PHARMACEUTICAL COMPOSITION CONTAINING PYRIDYLAMINOACETIC ACID COMPOUND

CROSS REFERENCE TO RELATED APPLICATIONS

The present application is a continuation under 35 U.S.C. § 120 of U.S. application Ser. No. 16/173,299, filed on Oct. 29, 2018 and which was a continuation of U.S. application Ser. No. 15/204,507, filed on Jul. 7, 2016, the entire contents of both of which are incorporated herein by reference and priority to which is hereby claimed. U.S. application Ser. No. 15/204,507 is a continuation under 35 U.S.C. § 120 of PCT/JP2015/050334 filed on Jan. 8, 2015, which is incorporated herein reference and which claimed priority to Japanese Application No. 2014-002810, filed Jan. 10, 2014, the entire content of which is also incorporated herein by reference.

TECHNICAL FIELD

The present invention relates to a pharmaceutical composition comprising isopropyl (6-{[4-(pyrazol-1-yl)benzyl](pyridin-3-ylsulfonyl)aminomethyl}pyridin-2-ylamino)acetate or a salt thereof, and a method for stabilizing the compound or salt thereof.

BACKGROUND ART

Isopropyl (6-{[4-(pyrazol-1-yl)benzyl](pyridin-3-ylsulfonyl)aminomethyl}pyridin-2-ylamino)acetate is a compound represented by the following formula (1):

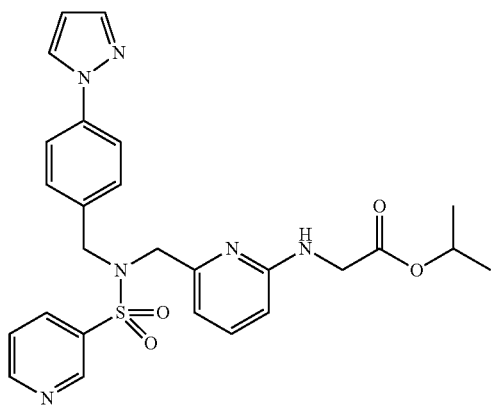

(1)

Patent Document 1 and Patent Document 2 mention pyridylaminoacetic acid compounds such as isopropyl (6-{[4-(pyrazol-1-yl)benzyl](pyridin-3-ylsulfonyl)aminomethyl}pyridin-2-ylamino)acetate, and Patent Document 1 mentions, as eye drops of the pyridylaminoacetic acid compound, Formulation Examples comprising concentrated glycerol and Polysorbate 80.

However, there is not mentioned a pharmaceutical composition comprising isopropyl (6-{[4-(pyrazol-1-yl)benzyl](pyridin-3-ylsulfonyl)aminomethyl}pyridin-2-ylamino)acetate or a salt thereof, which further comprises edetic acid or a salt thereof, and also there is absolutely no mention that stability of isopropyl (6-{[4-(pyrazol-1-yl)benzyl](pyridin-3-ylsulfonyl)aminomethyl}pyridin-2-ylamino)acetate or a salt thereof in the pharmaceutical composition, and preservative effectiveness of the pharmaceutical composition are improved.

Patent Document 1: U.S. Published Patent Application Publication, No. 2012/0190852, Specification
Patent Document 2: U.S. Published Patent Application Publication, No. 2011/0054172, Specification

DISCLOSURE OF THE INVENTION

Problems to be Solved by the Invention

At a stage of development of a pharmaceutical composition comprising isopropyl (6-{[4-(pyrazol-1-yl)benzyl](pyridin-3-ylsulfonyl)aminomethyl}pyridin-2-ylamino)acetate or a salt thereof (hereinafter also referred to as "the present compound"), the present inventors have found that, in an aqueous composition comprising the present compound dissolved therein, stability of the present compound is inferior.

An object of the present invention is to provide a pharmaceutical composition comprising the present compound, in which the present compound in the pharmaceutical composition is stable, the pharmaceutical composition having excellent preservative effectiveness. Another object of the present invention is to provide a method for improving stability of the present compound in the pharmaceutical composition, and preservative effectiveness of the pharmaceutical composition.

Means for Solving the Problems

The present inventors have intensively studied about additives in the composition comprising the present compound so as to achieve the above objects, and found that the present compound in a pharmaceutical composition has a high remaining rate even under long-term storage when further adding edetic acid or a salt thereof in the composition comprising the present compound, and that the pharmaceutical composition has excellent preservative effectiveness, thus completing the present invention. Namely, the present invention is related to the following.

(1) A pharmaceutical composition comprising isopropyl (6-{[4-(pyrazol-1-yl)benzyl](pyridin-3-ylsulfonyl)aminomethyl}pyridin-2-ylamino)acetate or a salt thereof, which further comprises edetic acid or a salt thereof.

(2) A pharmaceutical composition comprising isopropyl (6-{[4-(pyrazol-1-yl)benzyl](pyridin-3-ylsulfonyl)aminomethyl}pyridin-2-ylamino)acetate or a salt thereof and a nonionic surfactant, which further comprises edetic acid or a salt thereof (3) The pharmaceutical composition according to (2), wherein the nonionic surfactant includes polyoxyethylene castor oil, polyoxyethylene hardened castor oil, polyoxyethylene sorbitan fatty acid ester, or vitamin E TPGS.

(4) The pharmaceutical composition according to (3), wherein the polyoxyethylene castor oil includes polyoxyethylene castor oil selected from the group consisting of polyoxyl 5 castor oil, polyoxyl 9 castor oil, polyoxyl 15 castor oil, polyoxyl 35 castor oil, and polyoxyl 40 castor oil.

(5) The pharmaceutical composition according to (3), wherein the polyoxyethylene hardened castor oil includes polyoxyethylene castor oil selected from the group consisting of polyoxyethylene hardened castor oil 10, polyoxyethylene hardened castor oil 40, polyoxyethylene hardened castor oil 50, and polyoxyethylene hardened castor oil 60.

(6) The pharmaceutical composition according to (3), wherein the polyoxyethylene sorbitan fatty acid ester includes polyoxyethylene castor oil selected from the group consisting of Polysorbate 80, Polysorbate 60, Polysorbate 40, polyoxyethylene sorbitan monolaurate, polyoxyethylene sorbitan trioleate, and Polysorbate 65.

(7) The pharmaceutical composition according to any one of (2) to (6), wherein the content of the nonionic surfactant is in a range of 0.001 to 5% (w/v).

(8) The pharmaceutical composition according to (7), wherein the content of the nonionic surfactant is in a range of 0.8 to 2% (w/v).

(9) The pharmaceutical composition according to any one of (2) to (8), wherein the content of the nonionic surfactant is in a range of 1 to 20,000 parts by mass relative to 1 part by mass of 6-{[4-(pyrazol-1-yl)benzyl](pyridin-3-ylsulfonyl)aminomethyl}pyridin-2-ylamino)isopropyl acetate or a salt thereof.

(10) The pharmaceutical composition according to any one of (1) to (9), wherein the content of 6-{[4-(pyrazol-1-yl)benzyl](pyridin-3-ylsulfonyl)aminomethyl}pyridin-2-ylamino)isopropyl acetate or a salt thereof is in a range of 0.0001 to 0.10% (w/v).

(11) The pharmaceutical composition according to (10), wherein the content of 6-{[4-(pyrazol-1-yl)benzyl](pyridin-3-ylsulfonyl)aminomethyl}pyridin-2-ylamino)isopropyl acetate or a salt thereof is in a range of 0.001 to 0.003% (w/v).

(12) The pharmaceutical composition according to any one of (1) to (11), wherein the content of edetic acid or a salt thereof is in a range of 0.001 to 1% (w/v).

(13) The pharmaceutical composition according to (12), wherein the content of edetic acid or a salt thereof is in a range of 0.01 to 0.1% (w/v).

(14) The pharmaceutical composition according to any one of (1) to (13), wherein the content of edetic acid or a salt thereof is in a range of 0.1 to 1,000 parts by mass relative to 1 part by mass of 6-{[4-(pyrazol-1-yl)benzyl](pyridin-3-ylsulfonyl)aminomethyl}pyridin-2-ylamino)isopropyl acetate or a salt thereof

(15) The pharmaceutical composition according to any one of (1) to (14), which further comprises boric acid or a salt thereof, citric acid or a salt thereof, or acetic acid or a salt thereof

(16) The pharmaceutical composition according to any one of (1) to (15), which does not comprise sorbic acid.

(17) The pharmaceutical composition according to any one of (1) to (16), which is filled into a container made of polyethylene.

(18) The pharmaceutical composition according to any one of (1) to (17), for prevention or treatment of glaucoma or ocular hypertension, or for reduction of intraocular pressure.

(19) A method for stabilizing isopropyl (6-{[4-(pyrazol-1-yl)benzyl](pyridin-3-ylsulfonyl)aminomethyl}pyridin-2-ylamino)acetate or a salt thereof by allowing a pharmaceutical composition comprising isopropyl (6-{[4-(pyrazol-1-yl)benzyl](pyridin-3-ylsulfonyl)aminomethyl}pyridin-2-ylamino)acetate or a salt thereof to comprise edetic acid or a salt thereof

(20) A method for improving preservative effectiveness of a pharmaceutical composition comprising isopropyl (6-{[4-(pyrazol-1-yl)benzyl](pyridin-3-ylsulfonyl)aminomethyl}pyridin-2-ylamino)acetate or a salt thereof by allowing the pharmaceutical composition to comprise edetic acid or a salt thereof.

The respective structures of the above-mentioned (1) to (20) can be combined by optionally selecting two or more structures therefrom.

Effects of the Invention

According to the present invention, it is possible to provide a pharmaceutical composition in which the present compound in a pharmaceutical composition is stabilized over a long period of time, the pharmaceutical composition having excellent preservative effectiveness. The pharmaceutical composition of the present invention has enough safety as a pharmaceutical product. According to the present invention, it is also possible to provide a method for stabilizing the present compound in a pharmaceutical composition over a long period of time to thereby improve preservative effectiveness of the pharmaceutical composition. According to the present invention, it is also possible to provide a method for using edetic acid or a salt thereof so as to produce a pharmaceutical composition in which the present compound in the pharmaceutical composition is stabilized over a long period of time, the pharmaceutical composition having excellent preservative effectiveness.

Preferred Mode for Carrying Out the Invention

Embodiments of the present invention will be described in detail below.

It is possible to produce isopropyl (6-{[4-(pyrazol-1-yl)benzyl](pyridin-3-ylsulfonyl)aminomethyl}pyridin-2-ylamino)acetate or a salt thereof comprised in a pharmaceutical composition of the present invention in accordance with a conventional method in the technical field, such as a method mentioned in U.S. Published Patent Application Publication, No. 2012/0190852, Specification.

In the pharmaceutical composition of the present invention, a salt of isopropyl (6-{[4-(pyrazol-1-yl)benzyl](pyridin-3-ylsulfonyl)aminomethyl}pyridin-2-ylamino)acetate is not particularly limited as long as it is a pharmacologically acceptable salt. Specifically, there are exemplified inorganic acid salts such as hydrochlorides, hydrobromates, hydroiodides, nitrates, sulfates, or phosphates; or organic acid salts such as acetates, trifluoroacetates, benzoates, oxalates, malonates, succinates, maleates, fumarates, tartrates, citrates, methanesulfonates, ethanesulfonates, trifluoromethanesulfonates, benzenesulfonates, p-toluenesulfonates, glutamates, or aspartates. Preferably, hydrochlorides or trifluoroacetates are exemplified.

In the pharmaceutical composition of the present invention, the content of isopropyl (6-{[4-(pyrazol-1-yl)benzyl](pyridin-3-ylsulfonyl)aminomethyl}pyridin-2-ylamino)acetate or a salt thereof is not particularly limited. Specifically, the lower limit is preferably 0.0001% (w/v), more preferably 0.0003% (w/v), still more preferably 0.0005% (w/v), and yet still more preferably 0.001% (w/v). The upper limit is preferably 0.1% (w/v), more preferably 0.03% (w/v), still more preferably 0.01% (w/v), yet still more preferably 0.008% (w/v), even still more preferably 0.005% (w/v), and particularly preferably 0.003% (w/v). More specifically, the content is preferably in a range of 0.0001 to 0.1% (w/v), more preferably 0.0003 to 0.03% (w/v), still more preferably 0.0005 to 0.01% (w/v), yet still more preferably 0.001 to 0.008% (w/v), even still more preferably 0.001 to 0.005% (w/v), and most preferably 0.001 to 0.003% (w/v). Comparatively small content of the present compound may enable a reduction in amount of a surfactant (typically polyoxyethylene castor oil), which is required to dissolve the present compound, so that the content of the present compound is preferably less than 0.01% (w/v). When comprising a salt of isopropyl (6-{[4-(pyrazol-1-yl)benzyl](pyridin-3-ylsulfonyl)aminomethyl}pyridin-2-ylamino)acetate, it means that the content of isopropyl (6-{[4-(pyrazol-1-yl)benzyl](pyridin-3-ylsulfonyl)aminomethyl}pyridin-2-ylamino)acetate falls in the above range in a state where the salt is isolated.

In the pharmaceutical composition of the present invention, it is desired to mix surfactants so as to dissolve the present compound. It is possible to appropriately mix a cationic surfactant, an anionic surfactant, and a nonionic surfactant, which are usable as additives for a pharmaceutical product, in the pharmaceutical composition of the present invention as surfactants. Of these surfactants, a nonionic surfactant is preferable.

Examples of the cationic surfactant include alkylamine salt, alkylaminepolyoxyethylene adduct, fatty acid triethanolamine monoester salt, acylaminoethyldiethylamine salt, fatty acid polyamine condensate, alkyltrimethylammonium salt, dialkyldimethylammonium salt, alkyldimethylbenzylammonium salt, alkylpyridinium salt, acylaminoalkyl type ammonium salt, acylaminoalkylpyridinium salt, diacyloxyethylammonium salt, alkylimidazoline, 1-acylaminoethyl-2-alkylimidazoline, 1-hydroxylethyl-2-alkylimidazoline, and the like. Examples of the alkyldimethylbenzylammonium salt include benzalkonium chloride, cetalkonium chloride, and the like. Examples of the anionic surfactant include phospholipid, and the like; and examples of the phospholipid include lecithin, and the like.

Examples of the nonionic surfactant include polyoxyethylene castor oil, polyoxyethylene hardened castor oil, polyoxyethylene sorbitan fatty acid ester, Vitamin E TPGS, polyoxyethylene fatty acid ester, polyoxyethylene polyoxypropylene glycol, sucrose fatty acid ester, and the like. Of these surfactants, polyoxyethylene castor oil is preferable from a viewpoint of being capable of further improving stability.

It is possible to use, as the polyoxyethylene castor oil, various polyoxyethylene castor oils each exhibiting different number of polymerization of ethylene oxide. The number of polymerization of ethylene oxide is preferably in a range of 5 to 100, more preferably 20 to 50, particularly preferably 30 to 40, and most preferably 35. Specific examples of the polyoxyethylene castor oil include polyoxyl 5 castor oil, polyoxyl 9 castor oil, polyoxyl 15 castor oil, polyoxyl 35 castor oil, polyoxyl 40 castor oil, and the like, and polyoxyl 35 castor oil is most preferable.

It is possible to use, as the polyoxyethylene hardened castor oil, various polyoxyethylene hardened castor oils each exhibiting different number of polymerization of ethylene oxide. The number of polymerization of ethylene oxide is preferably in a range of 10 to 100, more preferably 20 to 80, particularly preferably 40 to 70, and most preferably 60. Specific examples of the polyoxyethylene hardened castor oil include polyoxyethylene hardened castor oil 10, polyoxyethylene hardened castor oil 40, polyoxyethylene hardened castor oil 50, polyoxyethylene hardened castor oil 60, and the like, and polyoxyethylene hardened castor oil 60 is most preferable.

Examples of the polyoxyethylene sorbitan fatty acid ester include Polysorbate 80, Polysorbate 60, Polysorbate 40, polyoxyethylene sorbitan monolaurate, polyoxyethylene sorbitan trioleate, Polysorbate 65, and the like, and Polysorbate 80 is most preferable.

Vitamin E TPGS is also referred to as tocopherol polyethylene glycol 1000 succinate ester.

Examples of the polyoxyethylene fatty acid ester include polyoxyl 40 stearate, and the like.

Examples of the polyoxyethylene polyoxypropylene glycol include polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol, polyoxyethylene (20) polyoxypropylene (20) glycol, and the like. Examples of the sucrose fatty acid ester include sucrose stearic acid ester, and the like.

In the pharmaceutical composition of the present invention, the content of the surfactant is not particularly limited. Specifically, the lower limit is preferably 0.001% (w/v), more preferably 0.01% (w/v), still more preferably 0.1% (w/v), particularly preferably 0.5% (w/v), and most preferably 0.8% (w/v). The upper limit is preferably 10% (w/v), more preferably 5% (w/v), still more preferably 4% (w/v), particularly preferably 3% (w/v), and most preferably 2% (w/v). More specifically, the content is preferably in a range of 0.001 to 10% (w/v), more preferably 0.01 to 5% (w/v), still more preferably 0.1 to 4% (w/v), particularly preferably 0.5 to 3% (w/v), and most preferably 0.8 to 2% (w/v). The above content is applied to any surfactant, and is particularly preferably for a nonionic surfactant.

In the pharmaceutical composition of the present invention, the content of the nonionic surfactant relative to 6-{[4-(pyrazol-1-yl)benzyl](pyridin-3-ylsulfonyl)aminomethyl}pyridin-2-ylamino)isopropyl acetate or a salt thereof is not particularly limited. Specifically, the lower limit of the content of the nonionic surfactant is preferably 1 part by mass, more preferably 10 parts by mass, still more preferably 50 parts by mass, yet still more preferably 100 parts by mass, and particularly preferably 200 parts by mass, relative to 1 part by mass of 6-{[4-(pyrazol-1-yl)benzyl](pyridin-3-ylsulfonyl)aminomethyl}pyridin-2-ylamino)isopropyl acetate or a salt thereof. The upper limit is preferably 20,000 parts by mass, more preferably 10,000 parts by mass, still more preferably 5,000 parts by mass, yet still more preferably 3,000 parts by mass, and particularly preferably 2,000 parts by mass. More specifically, the content of the nonionic surfactant is preferably in a range of 1 to 20,000 parts by mass, more preferably 10 to 10,000 parts by mass, still more preferably 50 to 5,000 parts by mass, particularly preferably 100 to 3,000 parts by mass, and most preferably 200 to 2,000 parts by mass, relative to 1 part by mass of 6-{[4-(pyrazol-1-yl)benzyl](pyridin-3-ylsulfonyl)aminomethyl}pyridin-2-ylamino)isopropyl acetate or a salt thereof.

In the pharmaceutical composition of the present invention, examples of the salt of edetic acid include monosodium edetate, disodium edetate, tetrasodium edetate, and the like.

In the pharmaceutical composition of the present invention, the content of edetic acid or a salt thereof is not particularly limited. Specifically, the lower limit of the content is preferably 0.001% (w/v), more preferably 0.005% (w/v), still more preferably 0.01% (w/v), and most preferably 0.02% (w/v). The upper limit of the content is preferably 1.0% (w/v), more preferably 0.5% (w/v), still more preferably 0.1% (w/v), and most preferably 0.05% (w/v). More specifically, the content of edetic acid or a salt thereof is preferably in a range of 0.001 to 1% (w/v), more preferably 0.005 to 0.5% (w/v), and most preferably 0.01 to 0.1% (w/v).

In the pharmaceutical composition of the present invention, the content of edetic acid or a salt thereof relative to 1 part by mass of 6-{[4-(pyrazol-1-yl)benzyl](pyridin-3-ylsulfonyl)aminomethyl}pyridin-2-ylamino)isopropyl acetate or a salt thereof is not particularly limited. Specifically, the lower limit of the content of edetic acid or a salt thereof is preferably 0.1 part by mass, more preferably 0.2 part by mass, still more preferably 0.5 part by mass, particularly preferably 1 part by mass, and most preferably 3 parts by mass, relative to 1 part by mass of 6-{[4-(pyrazol-1-yl)benzyl](pyridin-3-ylsulfonyl)aminomethyl}pyridin-2-ylamino)isopropyl acetate or a salt thereof. The upper limit is preferably 1,000 parts by mass, more preferably 500 parts by mass, still more preferably 200 parts by mass, particularly preferably 100 parts by mass, and most preferably 50 parts by mass. More specifically, the content of edetic acid or a salt thereof is preferably in a range of 0.1 to 1,000 parts by mass, more preferably 0.2 to 500 parts by mass, still more preferably 0.5 to 200 parts by mass, particularly preferably 1 to 100 parts by mass, and most preferably 3 to 50 parts by mass, relative to 1 part by mass of 6-{[4-(pyrazol-1-yl)benzyl](pyridin-3-ylsulfonyl)aminomethyl}pyridin-2-ylamino)isopropyl acetate or a salt thereof.

Additives can be optionally used in the pharmaceutical composition of the present invention, and it is possible to add, as additives, a buffer agent, a tonicity agent, a stabilizer, a preservative, an antioxidant, a high molecular weight polymer, and the like.

It is possible to mix the buffer agent, which is usable as additives for a pharmaceutical product, in the pharmaceutical composition of the present invention. Examples of the buffer agent include phosphoric acid or a salt thereof, boric acid or a salt thereof, citric acid or a salt thereof, acetic acid or a salt thereof, carbonic acid or a salt thereof, tartaric acid or a salt thereof, ε-aminocaproic acid, trometamol, and the like. From a viewpoint of buffering capacity in a weak acid region, the buffer agent is preferably boric acid or a salt thereof, citric acid or a salt thereof, or acetic acid or a salt thereof, and particularly preferably citric acid or a salt thereof. Examples of the phosphate include sodium phosphate, sodium dihydrogen phosphate, disodium hydrogen phosphate, potassium phosphate, potassium dihydrogen phosphate, dipotassium hydrogen phosphate, and the like; examples of the borate include borax, sodium borate, potassium borate, and the like; examples of the citrate include sodium acetate, disodium citrate, trisodium citrate, and the like; examples of the acetate include sodium acetate, potassium acetate, and the like; examples of the carbonate include sodium carbonate, sodium hydrogen carbonate, and the like; and examples of the tartrate include sodium tartrate, potassium tartrate, and the like. When the buffer agent is mixed in the pharmaceutical composition of the present invention, the content of the buffer agent can be appropriately adjusted according to the type of the buffer agent, and is preferably in a range of 0.001 to 10% (w/v), more preferably 0.01 to 5% (w/v), still more preferably 0.1 to 3% (w/v), and most preferably 0.2 to 2% (w/v).

It is possible to appropriately mix the tonicity agent, which is usable as additives for a pharmaceutical product, in the pharmaceutical composition of the present invention. Examples of the tonicity agent include an ionic tonicity agent, a nonionic tonicity agent, and the like. Examples of the ionic tonicity agent include sodium chloride, potassium chloride, calcium chloride, magnesium chloride, and the like; and examples of the nonionic tonicity agent include glycerol, propylene glycol, sorbitol, mannitol, and the like. When the tonicity agent is mixed in the pharmaceutical composition of the present invention, the content of the tonicity agent can be appropriately adjusted according to the type of the tonicity agent, and is preferably in a range of 0.01 to 10% (w/v), more preferably 0.02 to 7% (w/v), still more preferably 0.1 to 5% (w/v), particularly preferably 0.5 to 4% (w/v), and most preferably 0.8 to 3% (w/v).

It is possible to appropriately mix the stabilizer, which is usable as additives for a pharmaceutical product, in the pharmaceutical composition of the present invention. Examples of the stabilizer include sodium citrate, and the like. When the stabilizer is mixed in the pharmaceutical composition of the present invention, the content of the stabilizer can be appropriately adjusted according to the type of the stabilizer.

It is possible to appropriately mix the preservative, which is usable as additives for a pharmaceutical product, in the pharmaceutical composition of the present invention. Examples of the preservative include benzalkonium chloride, benzalkonium bromide, benzethonium chloride, sorbic acid, potassium sorbate, methyl paraoxybenzoate, propyl paraoxybenzoate, chlorobutanol, and the like. From a viewpoint of stability of 6-{[4-(pyrazol-1-yl)benzyl](pyridin-3-ylsulfonyl)aminomethyl}pyridin-2-ylamino)isopropyl acetate or a salt thereof, it is desired not to include sorbic acid. When the preservative is mixed in the pharmaceutical composition of the present invention, the content of the preservative can be appropriately adjusted according to the type of the preservative, and is preferably in a range of 0.0001 to 1% (w/v), more preferably 0.0005 to 0.1% (w/v), still more preferably 0.001 to 0.05% (w/v), and most preferably 0.002 to 0.01% (w/v).

It is possible to appropriately mix the antioxidant, which is usable as additives for a pharmaceutical product, in the pharmaceutical composition of the present invention. Examples of the antioxidant include ascorbic acid, tocopherol, dibutylhydroxytoluene, butylhydroxyanisole, sodium erythorbate, propyl gallate, sodium sulfite, and the like. When the antioxidant is mixed in the pharmaceutical composition of the present invention, the content of the antioxidant can be appropriately adjusted according to the type of the antioxidant, and is preferably in a range of 0.0001 to 1% (w/v), more preferably 0.0005 to 0.1% (w/v), still more preferably 0.001 to 0.02% (w/v), and most preferably 0.005 to 0.010% (w/v).

It is possible to appropriately mix the high molecular weight polymer, which is usable as additives for a pharmaceutical product, in the pharmaceutical composition of the present invention. Examples of the high molecular weight polymer include methyl cellulose, ethyl cellulose, hydroxymethyl cellulose, hydroxyethyl cellulose, hydroxypropyl cellulose, hydroxyethylmethyl cellulose, hydroxypropylmethyl cellulose, carboxymethyl cellulose, sodium carboxymethyl cellulose, hydroxypropylmethylcellulose acetate succinate, hydroxypropylmethylcellulose phthalate, carboxymethylethyl cellulose, cellulose acetate phthalate, polyvinylpyrrolidone, polyvinyl alcohol, carboxyvinyl polymer, polyethylene glycol, and the like. When the high molecular weight polymer is mixed in the pharmaceutical composition of the present invention, the content of the high molecular weight polymer can be appropriately adjusted according to the type of the high molecular weight polymer, and is preferably in a range of 0.001 to 5% (w/v), more preferably 0.01 to 1% (w/v), and still more preferably 0.1 to 0.5% (w/v).

The pH of the pharmaceutical composition of the present invention is preferably in a range of 4.0 to 8.0, more preferably 4.5 to 7.5, still more preferably 5.0 to 7.0, and most preferably 5.5 to 6.5.

The pharmaceutical composition of the present invention can be stored in a container made of various raw materials. For example, it is possible to use containers made of polyethylene, polypropylene, and the like. From a viewpoint of ease of instillation (hardness of container) and stability of the present compound, it is preferred to store in a container made of polyethylene.

The dosage form of the pharmaceutical composition of the present invention is not particularly limited as long as it is usable as a pharmaceutical product. Examples of the dosage form include eye drop, ophthalmic injection, and the like, and eye drop is particularly preferable. They can be produced in accordance with a conventional method in the technical field. The pharmaceutical composition of the present invention is basically a solution, and a solvent or dispersion medium thereof is preferably water.

The pharmaceutical composition of the present invention is useful for prevention or treatment of glaucoma or ocular hypertension, or for reduction of intraocular pressure. Examples of glaucoma in the present invention include primary open-angle glaucoma, secondary open-angle glaucoma, normal tension glaucoma, hypersecretion glaucoma, primary closed-angle glaucoma, secondary closed-angle glaucoma, plateau iris glaucoma, mixed glaucoma, developmental glaucoma, steroid glaucoma, exfoliation glaucoma, amyloid glaucoma, neovascular glaucoma, malignant glaucoma, capsular glaucoma, plateau iris syndrome, and the like.

The pharmaceutical composition of the present invention may comprise one or a plurality of, preferably 1 to 3 of, and more preferably one or two other glaucoma or ocular hypertension therapeutic agent(s) or intraocular tension depressor(s). The other glaucoma therapeutic agents is not particularly limited. Specifically, the other glaucoma therapeutic agent is preferably a commercially available glaucoma therapeutic agent or a glaucoma therapeutic agent under development, more preferably a commercially available glaucoma therapeutic agent, and particularly preferably a commercially available glaucoma therapeutic agent whose mechanism of action is different from that of the present compound. More specifically, there are exemplified a non-selective sympathomimetic agent, an α2 receptor agonist, an al receptor antagonist, a β receptor antagonist, a parasympatholytic agent, a carbonate dehydratase inhibitor, prostaglandins, a Rho kinase inhibitor, and the like.

Specific examples of the non-selective sympathomimetic agent include dipivefrin; specific examples of the α2 receptor agonist include brimonidine and apraclonidine; specific examples of the α1 receptor antagonist include bunazosin; specific examples of the β receptor antagonist include timolol, befunolol, carteolol, nipradilol, betaxolol, levobunolol, and metipranolol; specific examples of the parasympatholytic agent include pilocarpine; specific examples of the carbonate dehydratase inhibitor include dorzolamide, brinzolamide, and acetazolamide; specific examples of prostaglandins include latanoprost, isopropyl unoprostone, bimatoprost, and travoprost; and specific examples of the Rho kinase inhibitor include ripasudil.

EXAMPLES

Formulation Examples and test results will be shown below, but such are for better understanding of the present invention and do not limit the scope of the present invention.

Formulation Examples

Typical Formulation Examples using the present compound will be shown below. In the following Formulation Examples, the mixing amount of each component is the content in 100 mL of the composition.

Formulation Example 1

Eye drop (in 100 mL)
Present compound 0.001 g
Boric acid 0.2 g
Glycerol 2.0 g
Polysorbate 80 0.5 g
Disodium edetate 0.05 g
Benzalkonium chloride 0.005 g
Dilute hydrochloric acid q.s.
Sodium hydroxide q.s.
Purified water q.s.

Formulation Example 2

Eye drop (in 100 mL)
Present compound 0.001 g
Sodium dihydrogen phosphate 0.2 g
Glycerol 2.0 g
Vitamin E TPGS 0.8 g
Disodium edetate 0.05 g
Benzalkonium chloride 0.005 g
Dilute hydrochloric acid q.s.
Sodium hydroxide q.s.
Purified water q.s.

Formulation Example 3

Eye drop (in 100 mL)
Present compound 0.001 g
Trisodium citrate 0.2 g
Glycerol 2.0 g
Polyoxyethylene hardened castor oil 60 0.3 g
Disodium edetate 0.05 g
Benzalkonium chloride 0.005 g
Dilute hydrochloric acid q.s.
Sodium hydroxide q.s.
Purified water q.s.

Types and mixing amounts of the present compound, nonionic surfactant, edetic acid, and additives in Formulation Examples 1 to 3 can be appropriately adjusted to obtain desired compositions.

1. Stability Evaluation Test (1)

An influence of edetic acid on stability of the present compound was studied.

1-1. Preparation of Test Formulation

To 5 g of polyoxyl 35 castor oil, 20 mL of a 10% sodium dihydrogen phosphate solution, 10 mL of a 5% disodium edetate dihydrate solution, and 900 mL of purified water were added and dissolved. After adjusting the pH to about 6 by adding a sodium hydroxide solution or dilute hydrochloric acid (q.s.), 0.003 g of isopropyl (6-{[4-(pyrazol-1-yl)benzyl](pyridin-3-ylsulfonyl)aminomethyl}pyridin-2-ylamino)acetate (hereinafter also referred to as the compound A) was added and dissolved. To this was added purified water (q.s.) to make 1,000 mL in total, thus preparing a formulation of Example 1.

In the same manner as in preparation method of Example 1, formulations of Example 2 and Comparative Examples 1 to 2 shown in Table 1 were prepared.

1-2. Test Procedure

After filling a glass ampule with 5 mL of a test formulation and storing at 60° C. for an optional period, the content of isopropyl (6-{[4-(pyrazol-1-yl)benzyl](pyridin-3-ylsulfonyl)aminomethyl}pyridin-2-ylamino)acetate was determined using high-performance liquid chromatography, and then a remaining rate (%) thereof was calculated.

1-3. Test Results and Consideration

Test results are shown in Table 1.

TABLE 1

| | % (w/v) | | | |
|---|---|---|---|---|
| | Example 1 | Example 2 | Comparative Example 1 | Comparative Example 2 |
| Present compound A | 0.0003 | 0.0003 | 0.0003 | 0.0003 |
| Disodium edetate dihydrate | 0.05 | 0.05 | — | — |
| Polyoxyethylene hardened castor oil 60 | 0.5 | — | 0.5 | — |
| Polysorbate 80 | — | 0.5 | — | 0.5 |
| Sodium dihydrogen phosphate | 0.2 | 0.2 | 0.2 | 0.2 |
| HCl/NaOH | q.s. | q.s. | qs. | qs. |
| Purified water | q.s. | q.s. | qs. | qs. |

TABLE 1-continued

| | | % (w/v) | | | |
|---|---|---|---|---|---|
| | | Example 1 | Example 2 | Comparative Example 1 | Comparative Example 2 |
| pH | | 6.0 | 6.0 | 6.0 | 6.0 |
| Remaining rate(%) | 60° C./ 1 Week | 96.9 | 93.6 | 24.2 | 69.5 |

As is apparent from Table 1, the formulations of Examples 1 to 2 maintained significantly high remaining rate at 60° C. for a week, as compared with the formulations of Comparative Examples 1 and 2. The results revealed that the pharmaceutical composition of the present invention has excellent stability.

2. Stability Evaluation Test (2)

An influence of additives and pH in the pharmaceutical composition of the present invention was studied.

2-1. Preparation of Test Formulation

In the same manner as in preparation method of Example 1, the formulations of Examples 3 to 34 shown in Tables 2 to 8 were prepared.

2-2. Test Procedure

After filling a glass ampule with 5 mL of a test formulation and storing at 60° C. for an optional period, the content of isopropyl (6-{[4-(pyrazol-1-yl)benzyl](pyridin-3-ylsulfonyl)aminomethyl}pyridin-2-ylamino)acetate was determined using high-performance liquid chromatography, and then a remaining rate (%) thereof was calculated.

TABLE 2

| % (w/v) | | Example 3 | Example 4 | Example 5 | Example 6 | Example 7 |
|---|---|---|---|---|---|---|
| Present compound A | | 0.01 | 0.0003 | 0.001 | 0.01 | 0.03 |
| Polyoxyl 35 castor oil | | 0.8 | 0.5 | 0.8 | 2 | 2 |
| Sodium dihydrogen phosphate | | 0.2 | 0.2 | 0.2 | 0.2 | 0.2 |
| Disodium edetate dihydrate | | 0.01 | 0.05 | 0.05 | 0.05 | 0.05 |
| Glycerol | | 2.3 | — | 2.3 | 2.3 | 2.3 |
| Benzalkonium chloride | | 0.004 | — | 0.004 | 0.004 | 0.004 |
| HCl/NaOH | | q.s. | q.s. | q.s. | q.s. | q.s. |
| Purified water | | q.s. | q.s. | q.s. | q.s. | q.s. |
| pH | | 5.8 | 6.0 | 5.8 | 5.8 | 5.8 |
| Remaining rate(%) | 60° C./ 1 Week | 94.5 | ND | 93.02 | 94.0 | 94.1 |
| | 60° C./ 4 Weeks | 86.2 | 83.2 | 82.2 | 87.1 | 90.9 |

TABLE 3

| % (w/v) | Example 8 | Example 9 | Example 10 | Example 11 | Example 12 | Example 13 | Example 14 |
|---|---|---|---|---|---|---|---|
| Present compound A | 0.003 | 0.003 | 0.003 | 0.003 | 0.003 | 0.01 | 0.01 |
| Polyoxyl 35 castor oil | 0.8 | 0.8 | 0.8 | 0.8 | 0.8 | 0.8 | 0.8 |
| Sodium dihydrogen phosphate | 0.2 | — | — | — | — | — | — |
| Boric acid | — | 1 | — | — | — | 1 | — |
| Trisodium citratedihydrate | — | — | 0.2 | — | — | — | — |
| Sodium acetatetrihydrate | — | — | — | 0.2 | — | — | — |
| ε-Aminocaproic acid | — | — | — | — | 0.2 | — | — |
| Trometamol | — | — | — | — | — | — | 0.9 |

TABLE 3-continued

| % (w/v) | Example 8 | Example 9 | Example 10 | Example 11 | Example 12 | Example 13 | Example 14 |
|---|---|---|---|---|---|---|---|
| Disodium edetate dihydrate | 0.02 | 0.02 | 0.02 | 0.02 | 0.02 | 0.05 | 0.05 |
| Glycerol | 2.2 | 1.0 | 2.2 | 2.2 | 2.2 | 1.4 | 0.8 |
| Benzalkonium chloride | 0.004 | 0.004 | 0.004 | 0.004 | 0.004 | 0.004 | 0.004 |
| HCl/NaOH | q.s. | q.s. | q.s. | q.s. | q.s. | q.s. | q.s. |
| Purified water | q.s. | q.s. | q.s. | q.s. | q.s. | q.s. | q.s. |
| pH | 6.0 | 6.0 | 6.0 | 6.0 | 6.0 | 5.8 | 5.8 |
| Remaining rate (%) 60° C./2 Weeks | 94.6 | 94.0 | 95.1 | 94.3 | 94.4 | 93.1 | 92.6 |

TABLE 4

| | % (w/v) | | | |
|---|---|---|---|---|
| | Example 15 | Example 16 | Example 17 | Example 18 |
| Present compound A | 0.01 | 0.01 | 0.01 | 0.01 |
| Polyoxyl 35 castor oil | 0.8 | 0.8 | 0.8 | 0.8 |
| Sodium dihydrogen phosphate | 0.2 | 0.2 | 0.2 | 0.2 |
| Disodium edetate dihydrate | 0.05 | 0.05 | 0.05 | 0.05 |
| Glycerol | 2.3 | 2.3 | 2.3 | 2.3 |
| Benzalkonium chloride | 0.002 | 0.008 | 0.004 | 0.004 |
| HCl/NaOH | q.s. | q.s. | q.s. | q.s. |
| Purified water | q.s. | q.s. | q.s. | q.s. |
| pH | 5.8 | 5.8 | 5.0 | 6.5 |
| Remaining rate(%) 60° C./2 Weeks | 95.3 | 94.1 | 94.8 | 92.6 |

TABLE 5

| | % (w/v) | | | |
|---|---|---|---|---|
| | Example 19 | Example 20 | Example 21 | Example 22 |
| Present compound A | 0.003 | 0.003 | 0.003 | 0.003 |
| Polyoxyl 35 castor oil | 0.8 | 0.8 | 0.8 | 0.8 |
| Boric acid | 1 | 1 | — | — |
| ε-Aminocaproic acid | — | — | 0.2 | 0.2 |
| Disodium edetate dihydrate | 0.02 | 0.02 | 0.02 | 0.02 |
| Glycerol | 1 | — | 2.3 | — |
| Mannitol | — | 2.0 | — | 4.5 |
| Benzalkonium chloride | 0.0013 | 0.0013 | 0.0013 | 0.0013 |
| HCl/NaOH | q.s. | q.s. | q.s. | q.s. |
| Purified water | q.s. | q.s. | q.s. | q.s. |
| pH | 6.0 | 6.0 | 6.0 | 6.0 |
| Remaining rate(%) 60° C./2 Weeks | 93.3 | 93.0 | 93.4 | 93.6 |

TABLE 6

| % (w/v) | Example 23 | Example 24 | Example 25 | Example 26 | Example 27 | Example 28 | Example 29 |
|---|---|---|---|---|---|---|---|
| Present compound A | 0.0003 | 0.0003 | 0.0003 | 0.0003 | 0.0003 | 0.003 | 0.0003 |
| Polysorbate 80 | 0.5 | 0.5 | 0.5 | 0.5 | 0.5 | 0.8 | — |
| Vitamin E TPGS | — | — | — | — | — | — | 0.5 |
| Sodium dihydrogen phosphate | 0.2 | 0.2 | — | — | — | — | — |
| Boric acid | — | — | 1 | — | — | — | 1 |
| Sodium citratehydrate | — | — | — | 1 | — | — | — |
| Trometamol | — | — | — | — | 1 | — | — |
| Trisodium citratedihydrate | | | | | | 0.2 | |
| Disodium edetate dihydrate | 0.05 | 0.05 | 0.05 | 0.05 | 0.05 | 0.02 | 0.01 |
| Sodium chloride | 0.8 | — | — | — | — | — | — |
| Glycerol | — | 2.2 | — | — | — | 2.2 | 1.0 |
| Benzalkonium chloride | — | — | — | — | — | 0.004 | 0.01 |
| HCl/NaOH | q.s. | q.s. | q.s. | q.s. | q.s. | q.s. | q.s. |
| Purified water | q.s. | q.s. | q.s. | q.s. | q.s. | q.s. | q.s. |
| pH | 6.0 | 6.0 | 6.0 | 6.0 | 6.0 | 6.0 | 6.0 |
| Remaining rate (%) 60° C./2 Weeks | 93.8 | 95.3 | 96.0 | 93.7 | 96.1 | 94.0 | 86.0 |

TABLE 7

| | % (w/v) | | |
|---|---|---|---|
| | Example 30 | Example 31 | Example 32 |
| Present compound A | 0.0003 | 0.0003 | 0.0003 |
| Polysorbate 80 | 0.5 | 0.8 | 0.8 |
| ε-Aminocaproic acid | 0.2 | 0.2 | 0.2 |
| Disodium edetate dihydrate | 0.02 | 0.02 | 0.02 |
| Glycerol | — | 2.3 | — |
| Mannitol | 4.5 | — | 4.5 |
| Benzalkonium chloride | 0.0013 | 0.0013 | 0.0013 |
| HCl/NaOH | q.s. | q.s. | q.s. |
| Purified water | q.s. | q.s. | q.s. |
| pH | 6.0 | 6.0 | 6.0 |
| Remaining rate(%) 60° C./2 Weeks | 90.2 | 93.2 | 93.9 |

TABLE 8

| | % (w/v) | |
|---|---|---|
| | Example 33 | Example 34 |
| Present compoundA | 0.0003 | 0.0003 |
| Polyoxyl 35 castor oil | 0.8 | 0.8 |
| Boric acid | 1 | 1 |
| Sorbic acid | 0.1 | — |
| Disodium edetate dihydrate | 0.05 | 0.05 |
| Glycerol | 1 | 1 |
| Benzalkonium chloride | 0.01 | 0.01 |
| HCl/NaOH | q.s. | q.s. |
| Purified water | qs. | q.s. |
| pH | 6.5 | 6.5 |
| Remaining rate(%) 60° C./2 Weeks | 89.1 | 92.5 |

As is apparent from Tables 2 to 8, the formulations of Examples 3 to 34 maintained a high remaining rate at 60° C. over 2 or 4 weeks.

3. Preservative Effectiveness Evaluation Test

Preservative effectiveness of the pharmaceutical composition of the present invention was studied.

3-1. Preparation of Test Formulation

In the same manner as in preparation method of Example 1, the formulations of Examples 35 to 43 and Comparative Example 3 shown in Tables 9 and 10 were prepared.

TABLE 9

| | % (w/v) | | | | |
|---|---|---|---|---|---|
| | Example 35 | Example 36 | Example 37 | Example 38 | Example 39 |
| Present compound A | 0.003 | 0.0003 | 0.003 | 0.003 | 0.003 |
| Polyoxyl 35 castor oil | 0.8 | 0.8 | 0.8 | 0.2 | 0.8 |
| Boric acid | 1.0 | 1.0 | 1.0 | 1.0 | 1.0 |
| Disodium edetate dihydrate | 0.005 | 0.02 | 0.05 | 0.01 | 0.01 |
| Glycerol | 1.0 | 1.0 | 1.0 | 1.0 | 1.0 |
| Benzalkonium chloride | 0.0085 | 0.0085 | 0.0085 | 0.004 | 0.0085 |
| HCl/NaOH | q.s. | q.s. | q.s. | q.s. | q.s. |
| Purified water | q.s. | q.s. | q.s. | q.s. | q.s. |
| pH | 5.5 | 5.5 | 5.5 | 5.0 | 6.5 |

TABLE 10

| | % (w/v) | | | | |
|---|---|---|---|---|---|
| | Example 40 | Example 41 | Example 42 | Example 43 | Comparative Example 3 |
| Present compound A | 0.003 | 0.0003 | 0.001 | 0.003 | 0.003 |
| Polyoxyl 35 castor oil | 0.8 | 0.8 | 1.4 | — | 0.8 |
| Polysorbate 80 | — | — | — | 0.8 | — |
| Trisodium citratedihydrate | 0.2 | 0.2 | 0.14 | 0.2 | — |
| Citric acidmonohydrtae | — | — | 0.03 | — | — |
| Boric acid | — | — | — | — | 1.0 |
| Disodium edetate dihydrate | 0.02 | 0.02 | 0.02 | 0.02 | — |
| Glycerol | 2.2 | 2.2 | 2.3 | 2.2 | 1.0 |
| Benzalkonium chloride | 0.0085 | 0.004 | 0.0085 | 0.004 | 0.0085 |
| HCl/NaOH | q.s. | q.s. | q.s. | q.s. | q.s. |
| Purified water | q.s. | q.s. | q.s. | q.s. | q.s. |
| pH | 6.0 | 6.0 | 5.6 | 6.0 | 5.5 |

3-2. Test Procedure (Bacterial Strains)

The following strains were used as inoculum.

Bacteria:

*Escherichia coli, Escherichia coli* ATCC 8739

*Pseudomonas aeruginosa, Pseudomonas aeruginosa* ATCC 9027

*Staphylococcus aureus, Staphylococcus aureus* ATCC 6538

Yeast fungus and molds:

*Candida albicans, Candida albicans* ATCC 10231

*Aspergillus niger, Aspergillus niger* ATCC16404

(Test Procedure)

A test was performed in accordance with a preservative effectiveness test defined in Sixteenth Revised Japanese Pharmacopoeia. Namely, an inoculum solution was prepared so as to adjust the concentration in a range of $10^7$ to $10^8$ cfu/mL and each formulation of Examples 35 to 43 and Comparative Example 3 was aseptically inoculated with each inoculum solution so as to adjust the concentration in a range of $10^5$ to $10^6$ cfu/mL, followed by uniform mixing to give samples. These samples were stored under light-shielded condition at 20 to 25° C. and, after 14 and 28 days, 1 mL of each sample was collected and the number of general viable bacteria was measured.

The number of general viable bacteria of bacteria, yeast fungus, and molds was measured in accordance with a most probable number method defined in a microbial limit test of Sixteenth Revised Japanese Pharmacopoeia.

From the number of general viable bacteria determined by the most probable number method, a remaining rate was determined on the assumption that an initial bacterial count determined from the inoculum solution is 100.

(Judging Method)

The case where the number of general viable bacteria after 14 and 28 days satisfies criteria of Table 11 in all bacterial strains was judged as "Passed". When all results in each sampling are judged as "Passed", it was judged that "preservative effectiveness exists".

TABLE 11

| Sampling time | Bacteria | Yeast fungus and molds |
|---|---|---|
| After 14 days | 0.1% or less relative to inoculumnumber | Same level as that of inoculumnumber or less |
| After 28 days | Same level as that of inoculumnumber or less after 14 days | Same level as that of inoculumnumber or less |

3-3. Test Results and Consideration

Test results and judgements are shown in Table 12.

TABLE 12

Results and judgments of preservative effectiveness test

| | Bacterial strains | After 14 days | After 28 days | Judgment |
|---|---|---|---|---|
| Example 35 | Bacteria | Passed | Passed | Preservative effectiveness exists |
| | Yeast fungus and molds | Passed | Passed | |
| Example 36 | Bacteria | Passed | Passed | Preservative effectiveness exists |
| | Yeast fungus and molds | Passed | Passed | |
| Example 37 | Bacteria | Passed | Passed | Preservative effectiveness exists |
| | Yeast fungus and molds | Passed | Passed | |
| Example 38 | Bacteria | Passed | Passed | Preservative effectiveness exists |
| | Yeast fungus and molds | Passed | Passed | |
| Example 39 | Bacteria | Passed | Passed | Preservative effectiveness exists |
| | Yeast fungus and molds | Passed | Passed | |
| Example 40 | Bacteria | Passed | Passed | Preservative effectiveness exists |
| | Yeast fungus and molds | Passed | Passed | |
| Example 41 | Bacteria | Passed | Passed | Preservative effectiveness exists |
| | Yeast fungus and molds | Passed | Passed | |
| Example 42 | Bacteria | Passed | Passed | Preservative effectiveness exists |
| | Yeast fungus and molds | Passed | Passed | |
| Example 43 | Bacteria | Passed | Passed | Preservative effectiveness exists |
| | Yeast fungus and molds | Passed | Passed | |
| Comparative Example 3 | Bacteria | Not Passed | Passed | No preservative effectiveness exists |
| | Yeast fungus and molds | Passed | Passed | |

As is apparent from Table 12, the formulations of Examples 35 to 43 have preservative effectiveness which conforms to standards of a preservative effectiveness test defined in Sixteenth Revised Japanese Pharmacopoeia. These results revealed that the pharmaceutical composition of the present invention has excellent preservative effectiveness.

The invention claimed is:

1. A pharmaceutical composition comprising isopropyl (6-{[4-(pyrazol-1-yl)benzyl](pyridin-3-ylsulfonyl)aminomethyl}pyridin-2-ylamino)acetate or a salt thereof and a nonionic surfactant, which further comprises edetic acid or a salt thereof,
    wherein the nonionic surfactant includes polyoxyethylene castor oil,
    wherein the pharmaceutical composition does not comprise sorbic acid;
    wherein the content of the nonionic surfactant is in a range of 0.001 to 5% (w/v), and
    wherein the content of the edetic acid or a salt thereof is in a range of 0.001 to 1% (w/v).

2. The pharmaceutical composition according to claim 1, wherein the polyoxyethylene castor oil includes polyoxyethylene castor oil selected from the group consisting of polyoxyl 5 castor oil, polyoxyl 9 castor oil, polyoxyl 15 castor oil, polyoxyl 35 castor oil, and polyoxyl 40 castor oil.

3. The pharmaceutical composition according to claim 1, wherein the content of the nonionic surfactant is in a range of 0.5 to 3% (w/v).

4. The pharmaceutical composition according to claim 1, wherein the content of the nonionic surfactant is in a range of 1 to 20,000 parts by mass relative to 1 part by mass of isopropyl 6-{[4-(pyrazol-1-yl)benzyl](pyridin-3-ylsulfonyl) aminomethyl}pyridin-2-ylamino)acetate or a salt thereof.

5. The pharmaceutical composition according to claim 1, wherein the content of isopropyl 6-{[4-(pyrazol-1-yl)benzyl](pyridin-3-ylsulfonyl)aminomethyl}pyridin-2-ylamino)acetate or a salt thereof is in a range of 0.0001 to 0.1% (w/v).

6. The pharmaceutical composition according to claim 5, wherein the content of isopropyl 6-{[4-(pyrazol-1-yl)benzyl](pyridin-3-ylsulfonyl)aminomethyl}pyridin-2-ylamino)acetate or a salt thereof is in a range of 0.001 to 0.003% (w/v).

7. The pharmaceutical composition according to claim 1, wherein the content of edetic acid or a salt thereof is in a range of 0.01 to 0.1% (w/v).

8. The pharmaceutical composition according to claim 1, wherein the content of edetic acid or a salt thereof is in a range of 0.1 to 1,000 parts by mass relative to 1 part by mass of isopropyl 6-{[4-(pyrazol-1-yl)benzyl](pyridin-3-ylsulfonyl)aminomethyl}pyridin-2-ylamino)acetate or a salt thereof.

9. The pharmaceutical composition according to claim 1, which further comprises boric acid or a salt thereof, citric acid or a salt thereof, or acetic acid or a salt thereof.

10. The pharmaceutical composition according to claim 1, which is filled into a container made of polyethylene.

11. The pharmaceutical composition according to claim 1, for prevention or treatment of glaucoma or ocular hypertension, or for reduction of intraocular pressure.

12. A method for stabilizing isopropyl (6-{[4-(pyrazol-1-yl)benzyl](pyridin-3-ylsulfonyl)aminomethyl}pyridin-2-ylamino)acetate or a salt thereof comprising adding edetic acid or a salt thereof and polyoxyethylene castor oil into a pharmaceutical composition comprising isopropyl (6-{[4-(pyrazol-1-yl)benzyl](pyridin-3-ylsulfonyl)aminomethyl}pyridin-2-ylamino)acetate or a salt thereof,
    wherein the pharmaceutical composition does not comprise sorbic acid,
    wherein the content of the nonionic surfactant is in a range of 0.001 to 5% (w/v); and
    wherein the content of the edetic acid or a salt thereof is in a range of 0.001 to 1% (w/v).

\* \* \* \* \*